US012753153B2

(12) United States Patent
Martinez et al.

(10) Patent No.: US 12,753,153 B2
(45) Date of Patent: Oct. 6, 2026

(54) METHOD FOR PREPARING 2-HYDROXY-5-OXOPROLINE

(71) Applicant: Millennium Enterprises, Inc., Marietta, GA (US)

(72) Inventors: Rodolfo Martinez, Santa Fe, NM (US); Robert Blaskovic, Marietta, GA (US); David Rembert Glass, Santa Fe, NM (US); Clifford J Unkefer, Los Alamos, NM (US)

( * ) Notice: Subject to any disclaimer, the term of this patent is extended or adjusted under 35 U.S.C. 154(b) by 385 days.

(21) Appl. No.: 18/231,051

(22) Filed: Aug. 7, 2023

(65) Prior Publication Data

US 2025/0051274 A1 Feb. 13, 2025

(51) Int. Cl.
*C07D 207/38* (2006.01)
*B01J 27/232* (2006.01)

(52) U.S. Cl.
CPC .......... *C07D 207/38* (2013.01); *B01J 27/232* (2013.01)

(58) Field of Classification Search
CPC .................................................... C07D 207/38
See application file for complete search history.

(56) References Cited

U.S. PATENT DOCUMENTS

| | | | | |
|---|---|---|---|---|
| 6,288,240 B1 * | 9/2001 | Martinez | C07D 207/277 548/534 |
| 2003/0032149 A1 | 2/2003 | Lalonde | |
| 2009/0325270 A1 | 12/2009 | Vick et al. | |

OTHER PUBLICATIONS

S. D. Razumovskii , T. V. Grinevich & G. V. Korovina, "Reactivity of hydrogen peroxide with respect to ozone", Reactivity of hydrogen peroxide with respect to ozone | Russian Journal of Physical Chemistry B, vol. 5, pp. 797-799, (2011).
International Patent Application No. PCT/US24/16056, "PCT Notification of Transmittal of the Internatonal Search Report and the Written Opinion of the Internatoinal Searching Authority, or the Declaration (PCT Rule 44.1)", dated May 20, 2024.
International Patent Application No. PCT/US24/16056, PCT International Search Report (PCT Article 18 and Rules 43 and 44), dated May 20, 2024.
International Patent Application No. PCT/US24/16056, "PCT Written Opinion of the International Searaching Authority (PCT Rule 43.bis. 1)", dated May 20, 2024.

(Continued)

*Primary Examiner* — Valerie Rodriguez-Garcia
(74) *Attorney, Agent, or Firm* — Luis M. Ortiz; Kamit D. Lopez; KPPB LAW

(57) ABSTRACT

The compound 2-hydroxy-5-oxoproline salt can be used to produce an increase in carbon dioxide fixation, growth, dry weight, nutritional value (proteins and amino acids), nodulation and nitrogen fixation and photosynthetically derived chemical energy when applied to plants through their roots and/or through their foliar portions. The embodiments provide an improved chemical synthesis for this compound which is performed in a single step reaction using ozone with 2-pyrrolidone-5-carboxylic acid. The steps of dissolving Sodium 2-pyrrolidone-5-carboxylate in aqueous solution and reacting a molar excess of ozone with the aqueous solution of sodium 2-pyrrolidone-5-carboxylate at a temperature between 20° C. and 100° C. can be carried out such that sodium 2-hydroxy-5-oxoproline salt is formed.

18 Claims, 2 Drawing Sheets

(56) References Cited

OTHER PUBLICATIONS

European Patent Application No. 24170811.4 - 1102, "Extended Search Report", dated Oct. 18, 2024.
Thomas E. Duffy, Arthur J. L. Cooper, and Fernando Vergara, "Acid-Catalyzed Hydrolysis of Ketoglutarmic Acid", Bioorganic Chemistry 5, 351-366 (1976).
Arthur J. L. Cooper, and Alton Meister, "The Glutamine Transaminase Amidase Pathway", Jan. 1977.
Tomiko Kuhara, et al., "Urinary 2-hydroxy-5-oxoproline9 the lactam form of a-ketoglutaramate, is markedly increased in urea cycle disorders", Anal Biüanal Chem (2011) 400:1843-1851.

* cited by examiner

METHOD FOR PREPARING 2-HYDROXY-5-OXOPROLINE

FIELD OF THE INVENTION

Embodiments of the present invention are generally related to 2-hydroxy-5-oxoproline. More particularly, embodiments are related to methods for preparing 2-hydroxy-5-oxoproline salt. Embodiments are also related to the preparation of 2-hydroxy-5-oxoproline salt by dissolving Sodium 2-pyrrolidone-5-carboxylate in aqueous solution and reacting a molar excess of ozone with the aqueous solution of sodium 2-pyrrolidone-5-carboxylate at a temperature between 20° C. and 100° C. such that sodium 2-hydroxy-5-oxoproline is formed.

BACKGROUND OF THE INVENTION

The metabolite 2-hydroxy-5-oxoproline (2-oxoglutaramate) was discovered several decades ago in animal livers and kidneys and investigated in these tissues. A limited understanding of its function in animals was developed from these studies, in cells this material appears to be made by the physiologically irreversible transamination of glutamine. The compound appears to play a role in the regulation of tissue glutamine levels and in ammonia genesis, that is, the amide nitrogen in glutamine is a major Source of urinary ammonia. See, e.g., "The Glutamine Transaminase-co-Amidase Pathway" by Arthur J. L. Cooper and Alton Meister, CRC Critical Reviews in Biochemistry, pages 281-303, January 1977, and "Occurrence Of Glutamine-2-Oxoacid Transaminase Activity In The Blue Green Alga ANABAENACYLINDRICA" by Masayuki Ohmori et al., J. Gen Appl. Microbiol. 31, 171 (1985).

More recently, 2-hydroxy-5-oxoproline has been found to have significant effect on plant growth. See, e.g., "Use Of Prolines For Improving Growth And Other Properties Of Plants And Algae' by Pat J. Unkefer, Thomas J. Knight, and Rodolfo A. Martinez, U.S. Patent and Trademark Office Ser. No. 09/493,039, filed on Jan. 27, 2000, where the inventors describe the use of the chemical class of compounds known as prolines for improving plant properties and performance.

In the past, 2-hydroxy-5-oxoproline has been synthesized using enzymatic procedures which are slow and difficult to control. See, e.g., A. L. Cooper and Alton Meister, Supra.

The reaction of Fremy's Salt with glutamic acid to yield (21%) an a-ketoacid of glutamic acid is described in "Oxidation of a-Amino Acids and a-Hydroxy Acids By Fremy's Salt. A Model For Oxidases?" by Angel Garcia-Raso, J. Org. Chem. 51, 4285 (1986). More particularly, L-glutamic acid was used as the starting material.

The quantitative chemical synthesis for this 2-hydroxy-5-oxoproline has been performed in a single step reaction of Fremy's Salt with either glutamine or 2-pyrrolidone-5-carboxylic acid, as was described by one of the present inventors (Martinez) in U.S. Pat. No. 6,288,240, entitled "preparation of 2-hydroxy-5-oxoproline and analogs thereof", which was granted Sep. 11, 2001. A product was produced in near quantitative yield. However, this process produced a waste stream that prevented its use for the commercial production of 2-hydroxy-5-oxoproline.

What is needed is a process that does not produce any waste and can be used as the commercial product when produced.

SUMMARY OF THE EMBODIMENTS

The following summary is provided to facilitate an understanding of some of the features of the disclosed embodiments and is not intended to be a full description. A full appreciation of the various aspects of the embodiments disclosed herein can be gained by taking the specification, claims, drawings, and abstract as a whole.

In accordance with a feature of the embodiments, a method is provided for preparing 2-hydroxy-5-oxoproline salt that includes the steps of: dissolving Sodium 2-pyrrolidone-5-carboxylate in aqueous solution and reacting a molar excess of ozone with the aqueous solution of sodium 2-pyrrolidone-5-carboxylate at a temperature between 20° C. and 50° C. such that sodium 2-hydroxy-5-oxoproline salt is formed.

In accordance with another feature of the embodiments, an aqueous solution of hydrogen peroxide can be reacted with the said solution of sodium 2-pyrrolidone-5-carboxylate at a temperature between 20° C. and 100° C.

In accordance with yet another feature of the embodiments, a method for preparing 2-hydroxy-5-oxoproline can further include the step of adjusting the pH of an aqueous solution of 2-pyrrolidone-5-carboxylic acid to pH7 with alkali metal hydroxides (i.e., sodium hydroxide, potassium hydroxide, calcium hydroxide, etc.).

In accordance with another feature of the embodiments, a method for preparing 2-hydroxy-5-oxoproline can further include the steps of adjusting the pH of an aqueous solution of 2-pyrrolidone-5-carboxylic acid to pH7 with alkali metal carbonates or bicarbonates (i.e., sodium carbonate, potassium carbonate, sodium bicarbonate, potassium bicarbonate, etc.).

These and other aspects of the embodiments will become more apparent in light of the detailed specification and drawings that follow.

SUMMARY OF THE DRAWINGS

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other issues, subject matter may be embodied as methods, devices, components, or systems. Accordingly, embodiments may, for example, take the form of hardware, software, firmware, or a combination thereof. The following detailed description is, therefore, not intended to be interpreted in a limiting sense.

Figure 1:
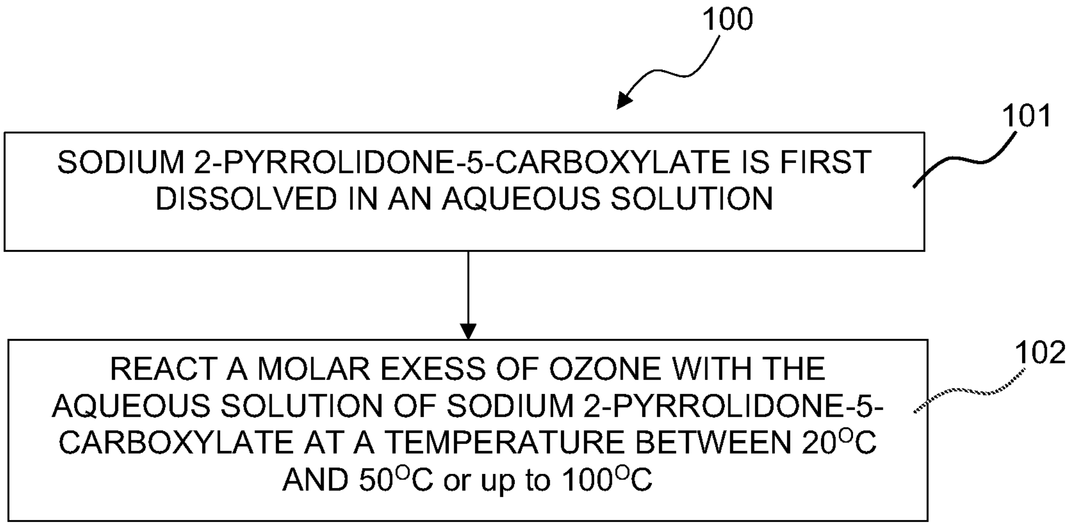
FIG. 1 illustrates a flow diagram of a method for preparing 2-hydroxy-5-oxoproline, in accordance with the embodiments.
Figure 2:
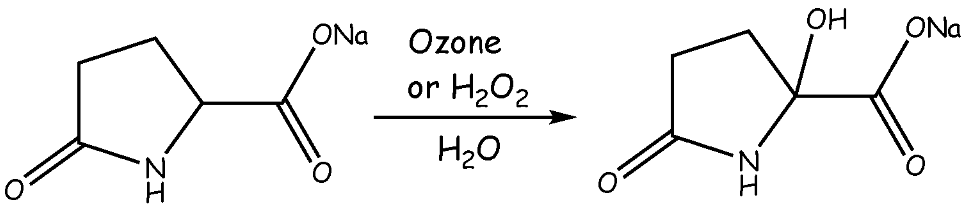
FIG. 2 illustrates a diagram of the reaction of pyroglutamic acid with alkali bases.

In accordance with a feature of the embodiments, a method is disclosed for preparing 2-hydroxy-5-oxoproline. Referring to FIG. 1 a flow diagram 100 of preparing 2-hydroxy-5-oxoproline is illustrated. Referring to block 101, sodium 2-pyrrolidone-5-carboxylate is first dissolved in an aqueous solution. Then a molar excess of ozone is allowed to react with the aqueous solution of sodium 2-pyrrolidone-5-carboxylate at a temperature between 20° C. and 50° C. such that sodium 2-hydroxy-5-oxoproline is formed, as show in in Block 102. Referring to FIG. 2, illustrated is a diagram of a reaction of pyroglutamic acid with an alkali bases.

Figure 3:
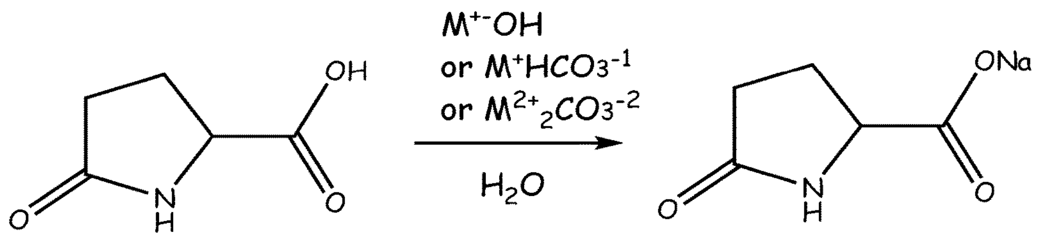
FIG. 3 illustrates a diagram of a complete reaction sequence which can be done in a single vessel; the 2-hydroxy-5-oxoproline salt that results from the method described herein, in accordance with the embodiments

Referring to FIG. 3, illustrated is a diagram of a complete reaction sequence which can be carried out in a single vessel. What is also shown is the 2-hydroxy-5-oxoproline salt that can result from the method described herein, in accordance with the embodiments.

Figure 4:
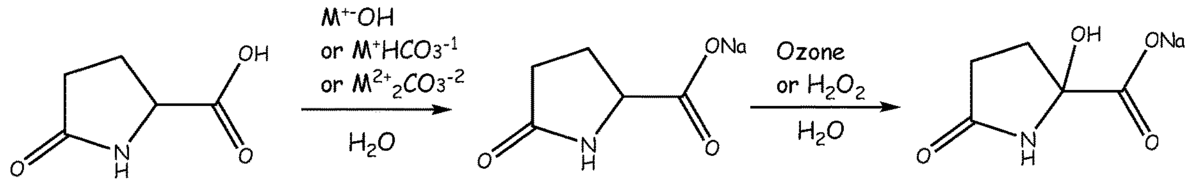
FIG. 4 illustrates a diagram of a complete reaction sequence that can be done in a single vessel, in accordance with the embodiments.

FIG. 4 illustrates another diagram of a complete reaction sequence that can be done in a single vessel, in accordance with the embodiments.

EXAMPLE: sodium L-glutamic acid or sodium L-pyroglutamic acid was reacted with an oxidant such as hydrogen peroxide or ozone. The reaction is allowed to proceed until the 4-hydroxypyroglutamic acid, sodium salt is formed. A typical reaction can be done as follows. Sodium pyroglutamate (20.4 g, 0.13 moles) was dissolved in water (100 mL). The homogenous colorless solution (pH=7) can be placed in an ambient temperature water bath to dissipate any heat produced in the reaction. The desired product can be synthesized using several radical reagents such as hydrogen peroxide ($H_2O_2$) and Ozone. The NMR and HPLC data are as follow:

NMR Data:

4-hydroxypyroglutamic acid, sodium salt $^{13}C$ NMR ($H_2O$ (unlocked), 75 MHz): δ=29, 34, 89, 177, 181

HPLC (ICSep ICE-ION-300 Column) (1% $H_2SO_4$, 0.4 mL/min) r.t.=20.817 min

In this example ozone was bubbled through the solution at 2 L/min for a total of 21 hours monitoring the disappearance of the SM (chemical shift=61 ppm) and subsequent appearance of the desired product (chemical shift=89 ppm). After this period nitrogen gas can be passed bubbled in the solution to remove excess ozone. An NMR analysis shows the expected 4-hydroxypyroglutamic acid, sodium salt and small amounts of by-products, succinimide and succinic acid sodium salt.

Another example of a typical scaled reaction is as follows: Sodium pyroglutamate (20.4 g, 0.13 moles) was dissolved in water (100 mL). The homogenous colorless solution (pH=7) was placed in an ambient temperature water bath to dissipate any heat produced in the reaction. The desired product has been synthesized using several radical reagents such as hydrogen peroxide ($H_2O_2$) and Ozone. In this example ozone was bubbled through the solution at 2 L/min for a total of 21 hours monitoring the disappearance of the SM (chemical shift=61 ppm) and subsequent appearance of the desired product (chemical shift=89 ppm). After this period nitrogen gas is passed bubbled in the solution to remove excess ozone. An NMR analysis shows that the expected 4-hydroxypyroglutamic acid, sodium salt and small amounts of by-products, succinimide and succinamic acid sodium salt.

It can be appreciated that the reaction can be scaled to multikilogram quantities by using a larger ozone generator and larger reactors.

A typical scaled reaction produced 140 Kg of product in 12-13 days of reaction time. The reaction rate can be increased or decreased by regulating the amount of ozone that is introduced to the reaction. Once the reaction is complete, compressed air is bubbled into the reaction to remove excess ozone. The product is used as produced without further purification.

It will be appreciated that variations of the above-disclosed embodiments and examples and other features and functions, or alternatives thereof, may be desirably combined into many other different systems or applications. It will also be appreciated that various presently unforeseen or unanticipated alternatives, modifications, variations, or improvements therein may be subsequently made by those skilled in the art which are also intended to be encompassed by the following claims.

What is claimed is:

1. A method for preparing 2-hydroxy-5-oxoproline salt, the method comprising the steps of:

(a) dissolving sodium 2-pyrrolidone-5-carboxylate in an aqueous solution; and (b) reacting a molar excess of ozone with the aqueous solution and sodium 2-pyrrolidone-5-carboxylate at a temperature between 20° C. and 50° C. such that sodium 2-hydroxy-5-oxoproline is formed.

2. The method for preparing 2-hydroxy-5-oxoproline salt as described in claim 1, wherein the aqueous solution is hydrogen peroxide and is reacted with the sodium 2-pyrrolidone-5-carboxylate.

3. The method for preparing 2-hydroxy-5-oxoproline salt as described in claim 1, further including the step of adjusting the pH of the aqueous solution and 2-pyrrolidone-5-carboxylate to pH7 with alkali metal hydroxides.

4. The method for preparing 2-hydroxy-5-oxoproline salt as described in claim 3, wherein the alkali metal hydroxides are selected from the group consisting of: sodium hydroxide, potassium hydroxide, and calcium hydroxide.

5. The method for preparing 2-hydroxy-5-oxoproline salt as described in claim 2, further including the step of adjusting the pH of the aqueous solution and 2-pyrrolidone-5-carboxylate to pH7 with alkali metal hydroxides.

6. The method for preparing 2-hydroxy-5-oxoproline salt as described in claim 5, wherein the alkali metal hydroxides are selected from the group consisting of: sodium hydroxide, potassium hydroxide, and calcium hydroxide.

7. The method for preparing 2-hydroxy-5-oxoproline salt as described in claim 1, further including the step of adjusting the pH of the aqueous solution and 2-pyrrolidone-5-carboxylate to pH7 with alkali metal carbonates or bicarbonates.

8. The method for preparing 2-hydroxy-5-oxoproline salt as described in claim 7, wherein the alkali metal carbonates or bicarbonates are selected from the group consisting of: sodium carbonate, potassium carbonate, sodium bicarbonate, and potassium bicarbonate.

9. The method for preparing 2-hydroxy-5-oxoproline salt as described in claim 2, further including the step of adjusting the pH of the aqueous solution and 2-pyrrolidone-5-carboxylate to pH7 with alkali metal carbonates or bicarbonates.

10. The method for preparing 2-hydroxy-5-oxoproline salt as described in claim 9, wherein the alkali metal carbonates or bicarbonates are selected from the group consisting of: sodium carbonate, potassium carbonate, sodium bicarbonate, and potassium bicarbonate.

11. A method for preparing 2-hydroxy-5-oxoproline salt, the method comprising the steps of:

(a) dissolving sodium 2-pyrrolidone-5-carboxylate in hydrogen peroxide; and (b) reacting a molar excess of ozone with the hydrogen peroxide and sodium 2-pyrrolidone-5-carboxylate at a temperature between 20° C. and 100° C. such that sodium 2-hydroxy-5-oxoproline is formed.

12. The method for preparing 2-hydroxy-5-oxoproline salt as described in claim 11, further including the step of adjusting the pH of the hydrogen peroxide and 2-pyrrolidone-5-carboxylate to pH7 with alkali metal hydroxides.

13. The method for preparing 2-hydroxy-5-oxoproline salt as described in claim 12, wherein the alkali metal hydroxides are selected from the group consisting of: sodium hydroxide, potassium hydroxide, and calcium hydroxide.

14. A method for preparing 2-hydroxy-5-oxoproline salt, the method comprising the steps of:

(a) dissolving sodium 2-pyrrolidone-5-carboxylate in an aqueous solution;

(b) reacting a molar excess of ozone with the aqueous solution and sodium 2-pyrrolidone-5-carboxylate at a temperature between 20° C. and 50° C. such that sodium 2-hydroxy-5-oxoproline is formed; and (c) adjusting the pH of the aqueous solution and 2-pyrrolidone-5-carboxylate to pH7 with at least one of alkali metal hydroxides, alkali metal carbonates or alkali metal bicarbonates.

15. The method for preparing 2-hydroxy-5-oxoproline salt as described in claim 14, wherein the alkali metal hydroxides are selected from the group consisting of: sodium hydroxide, potassium hydroxide, and calcium hydroxide.

16. The method for preparing 2-hydroxy-5-oxoproline salt as described in claim 14, wherein the alkali metal carbonates or bicarbonates are selected from the group consisting of: sodium carbonate, potassium carbonate, sodium bicarbonate, and potassium bicarbonate.

17. The method for preparing 2-hydroxy-5-oxoproline salt as described in claim 14, wherein the aqueous solution is hydrogen peroxide and is reacted with the sodium 2-pyrrolidone-5-carboxylate.

18. The method for preparing 2-hydroxy-5-oxoproline salt as described in claim 17, wherein the alkali metal carbonates or bicarbonates are selected from the group consisting of: sodium carbonate, potassium carbonate, sodium bicarbonate, and potassium bicarbonate.

* * * * *